United States Patent [19]

Shoesmith, deceased et al.

[11] Patent Number: Plant 6,839

[45] Date of Patent: Jun. 6, 1989

[54] CHRYSANTHEMUM PLANT NAMED VENETIAN

[75] Inventors: Leonard H. Shoesmith, deceased, late of Westfield, England, by May V. Shoesmith, executrix; Peter S. Hesse, Bradenton, Fla.

[73] Assignee: Ball Seed Company, Chicago, Ill.

[21] Appl. No.: 150,065

[22] Filed: Jan. 29, 1988

[51] Int. Cl.[4] ..... A01H 5/00

[52] U.S. Cl. ..... Plt./77

[58] Field of Search ..... Plt./77

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Venetian having small, clear white decorative pompom flowers, which are sturdy and crush resistant, long and rigid peduncles, nine week flower response, excellent suitability for winter production, and good storage characteristics of cut flowering stems.

1 Drawing Sheet

The present invention comprises a new and distinct cultivar of *Dendranthema grandiflora,* hereinafter referred to by the cultivar name Venetian.

Venetian is a product of a planned breeding program which had the objective of creating new Chrysanthemum cultivars with clear white decorative flowers, long peduncles, excellent keeping quality, and good performance under cool and low light growing conditions. Such traits in combination were not present or needed improvement in previously available commercial cultivars.

Venetian was originated from a hybridization made by Leonard H. Shoesmith in a controlled breeding program in Westfield-Woking, England in 1980. The male and female parents of Venetian are unknown. Venetian was discovered and selected as one flowering plant within the progeny of the stated cross by Peter S. Hesse in November 1981 in a controlled environment in Parrish, Fla.

The first act of asexual reproduction of Venetian was accomplished when vegetative cuttings were taken from the initial selection in March 1982 in a controlled environment in Parrish, Fla. by a technician working under formulations established and supervised by Peter S. Hesse. Horticultural examination of selected units initiated in September 1982 has demonstrated that the combination of characteristics as herein disclosed for Venetian are firmly fixed and are retained through successive generations of asexual reproduction.

Venetian has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

The following traits have been repeatedly observed and are determined to be basic characteristics of Venetian, which in combination distinguish this Chrysanthemum as a new and distinct cultivar:

1. Small, clear white decorative pompom.
2. When grown under warm temperatures, the immature ray florets appear pale yellow (R.H.S. 3C).
3. When grown under cooler temperatures, the immature ray florets appear creamy white (R.H.S. 155A).

4. Approximately 268 ray florets per capitulum.
5. Ray florets range from 2–3.1 cm long and 11–15 mm wide.
6. Overall flower diameter is 6–7 cm.
7. Flowers are very sturdy and resist crushing.
8. Peduncles are long and rigid.
9. Nine week flower response.
10. Performs well year round; particularly well suited for winter production, but not recommended for high temperatures.
11. Cut flowering stems store very well.

Of the many commercial cultivars known to the present inventors, the most similar in comparison to Venetian is Polaris. Reference is made to Chart A which compares certain characteristics of Venetian to those same characteristics of Polaris. In comparison to Polaris, Venetian has smaller flowers, one week faster flowering response, and fewer and less deep ray florets. The flower color and temperature response characteristics of Venetian are similar to those same characteristics of Polaris.

The accompanying photographic drawing shows typical inflorescence and foliage characteristics of Venetian, with colors being as nearly true as possible with illustrations of this type. The photograph is in black and white, with a few flowers being colored to show the white mature and the pale yellow immature ray florets.

In the following description, color references are made to The Royal Horticultural Society Colour Chart. The color values were determined between 10:00 and 10:30 a.m. on Jan. 4, 1988 under fluorescent lighting at Parrish, Fla.

Classification:

*Botanical.*—*Dendranthema grandiflora,* cv. Venetian.

*Commercial.*—Decorative pompom.

INFLORESCENCE

A. Capitulum:

*Form.*—Flat.

*Type.*—Double.

*Diameter across face.*—6–7 cm.

B. Corolla of ray florets:

*Color (general tonality from a distance of three meters).*—White.

*Color (upper surface).*—155D.
*Color (under surface).*—155D.

C. Corolla of disc florets: Very few present.
*Color (mature).*—Yellow.
*Color (immature).*—Yellow-green.

D. Reproductive organs:
*Androecium.*—Present in disc florets only.
*Gynoecium.*—Present in both disc and ray florets.

PLANT

A. General appearance:
*Height.*—Approximately 100 cm when grown unpinched and given 2 weeks of long days before short days begin.

B. Foliage:
*Color (upper surface).*—147A.
*Color (under surface).*—147B.

*Shape.*—Ovate, with incised margins.

CHART A

| | Venetian | Polaris |
|---|---|---|
| Mature ray floret color | 155D | 155D |
| Flower diameter | 6–7 cm | 7.5–9.5 cm |
| Ray floret length | 2–3.1 cm | 1.5–4.5 cm |
| Ray floret width | 11–15 mm | 8–18 mm |
| Average number of ray florets | 268 | 303 |
| Fully opened flower depth | 3–3.5 cm | 4–5 cm |
| Flower response | 9 weeks | 10 weeks |

It is claimed:

1. A new and distinct cultivar of Chrysanthemum plant named Venetian, as illustrated and described, and parts thereof.

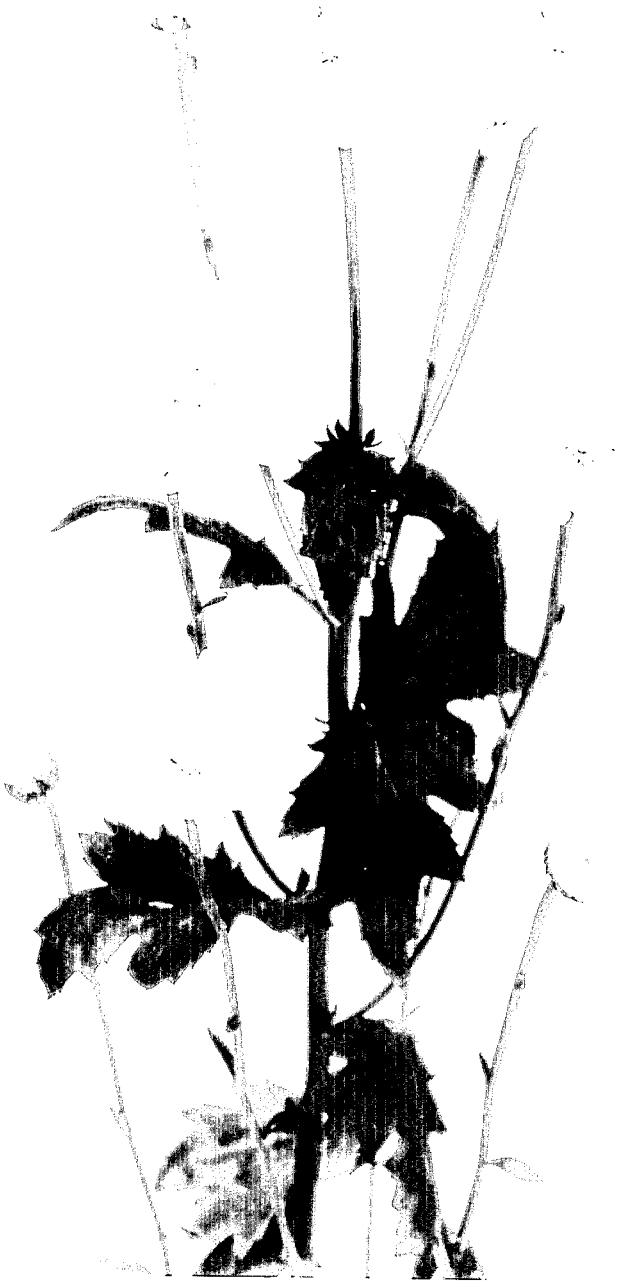

* * * * *